US012702751B2

(12) United States Patent
Yang

(10) Patent No.: US 12,702,751 B2
(45) Date of Patent: Aug. 11, 2026

(54) INTERLOCKING DRUG INFUSION DEVICE AND ARTIFICIAL PANCREAS

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 566 days.

(21) Appl. No.: 18/270,227

(22) PCT Filed: Jan. 24, 2022

(86) PCT No.: PCT/CN2022/073494
§ 371 (c)(1),
(2) Date: Jun. 29, 2023

(87) PCT Pub. No.: WO2022/148487
PCT Pub. Date: Jul. 14, 2022

(65) Prior Publication Data

US 2024/0316259 A1 Sep. 26, 2024

(30) Foreign Application Priority Data

Jan. 5, 2021 (WO) ................ PCT/CN2021/070207
Sep. 10, 2021 (WO) ................ PCT/CN2021/117647

(51) Int. Cl.
*A61M 5/142* (2006.01)

(52) U.S. Cl.
CPC .................. *A61M 5/14248* (2013.01); *A61M 2005/14268* (2013.01); *A61M 2205/8206* (2013.01)

(58) Field of Classification Search
CPC .... A61M 5/14248; A61M 2005/14268; A61M 2205/8206
See application file for complete search history.

(56) References Cited

U.S. PATENT DOCUMENTS

2013/0006194 A1* 1/2013 Anderson ............... A61M 5/31 604/218
2017/0203030 A1* 7/2017 Brewer ............ A61M 5/14244
(Continued)

FOREIGN PATENT DOCUMENTS

CA 2353275 1/2002
CN 104958077 10/2015
(Continued)

OTHER PUBLICATIONS

Translation of CN111939371 (Year: 2026).*
"International Search Report (Form PCT/ISA/210) of PCT/CN2022/073494," mailed on Apr. 19, 2022, pp. 1-3.

*Primary Examiner* — Dung T Ulsh
(74) *Attorney, Agent, or Firm* — JCIP GLOBAL INC.

(57) ABSTRACT

An interlocking drug infusion device includes a drug reservoir, used for accommodating the drug to be infused, provided with a piston and a screw; a driving wheel, connected with the screw, driving the screw to push the piston forward by rotation; a driving unit, the driving unit moved in a driving direction to drive the driving wheel to rotate; an actuator, electrically connected to the driving unit, used to provide power for the driving unit in the driving direction after energized; a program module, electrically connected to the actuator, the program module providing a first driving instruction for controlling the actuator to perform periodic power output; and a position detection module, used to determine the periodic drug infusion amount. When the drug infusion amount reaches a preset threshold, the position detection module and/or the program module provide the actuator with a second driving instruction.

17 Claims, 4 Drawing Sheets

(56) References Cited

U.S. PATENT DOCUMENTS

2019/0022313 A1* 1/2019 Barmaimon ...... A61M 5/31501
2020/0238099 A1* 7/2020 Madugula ............. G16H 20/17

FOREIGN PATENT DOCUMENTS

| CN | 108261591 | 7/2018 |
|---|---|---|
| CN | 110621366 | 12/2019 |
| CN | 111939371 | 11/2020 |
| CN | 111939387 | 11/2020 |

* cited by examiner

INTERLOCKING DRUG INFUSION DEVICE AND ARTIFICIAL PANCREAS

CROSS-REFERENCE TO RELATED APPLICATION

This application is a 371 of international application of PCT application serial no. PCT/CN2022/073494, filed on Jan. 24, 2022, which claims the priority benefit of PCT application no. PCT/CN2021/070207, filed on Jan. 5, 2021, and PCT application no. PCT/CN2021/117647, filed on Sep. 10, 2021. The entirety of each of the above mentioned patent applications is hereby incorporated by reference herein and made a part of this specification.

TECHNICAL FIELD

The present invention mainly relates to the field of medical instruments, in particular to an interlocking drug infusion device and the artificial pancreas thereof.

BACKGROUND

In a healthy person, the pancreas can automatically monitor the amount of glucose in the blood and automatically secrete the required dosage of insulin/glucagon. However, for diabetic patients, the function of their pancreas has been severely compromised, and the pancreas cannot secrete the required dosage of insulin. Therefore, diabetes mellitus is defined as a metabolic disease caused by abnormal pancreatic function, and it is also classified as one of the top three chronic conditions by the WHO. The present medical advancement has not been able to find a cure for diabetes mellitus. Yet, the best the technology could do is control the onset symptoms and complications by stabilizing the blood glucose level for diabetes patients.

Diabetic patients on an insulin pump need to check their blood glucose before infusing insulin into their bodies. At present, most detection methods can continuously detect blood glucose and send the blood glucose data to the remote device in real-time for the user to view. This detection method is called Continuous Glucose Monitoring (CGM), which requires the detection device to be attached to the surface of the patients' skin, and the sensor carried by the device to be inserted into the interstitial fluid for testing. According to the blood glucose (BG) level, the infusion system mimics an artificial pancreas to fill the gaps of the required insulin amount via the closed-loop pathway or the semi-closed-loop pathway.

However, the conventional drug infusion device is drived by a DC motor combined with a gear box and an encoder. Once the encoder fails, the drug infusion will be completely out of control, which cause excessive infusion and resulting in a potential risk of hypoglycemia and coma. The current drug infusion device uses a control program to control the driving mode of the linear actuator. Once the control program or electronic components fail, the drug infusion will be completely out of control, which also will result in a potential risk of hypoglycemia and coma. Therefore, there is an urgent need for a drug infusion device which can ensure the infusion safety when the control program or electronic components fail in the prior art.

BRIEF SUMMARY OF THE INVENTION

The invention discloses an interlocking drug infusion device. The program module in the drug infusion device provides a first driving instruction for controlling the actuator to perform periodic power output, and the position detection module in the infusion device is used to determine the periodic drug infusion amount. When the drug infusion amount reaches the preset threshold, the position detection module and/or program module provides the actuator with a second driving instruction. The program module and the position detection module physically form a synchronous interlock mechanism to prevent over-infusion in the event of failure of electronic components or preset programs, avoiding the risk of hypoglycemia or even coma.

The invention discloses an interlocking drug infusion device that includes a drug reservoir, used for accommodating the drug to be infused, provided with a piston and a screw; a driving wheel, connected with the screw, driving the screw to push the piston forward by rotation; a driving unit, the driving unit moved in a driving direction to drive the driving wheel to rotate; an actuator, electrically connected to the driving unit, used to provide power for the driving unit in the driving direction after energized; a program module, electrically connected to the actuator, the program module providing a first driving instruction for controlling the actuator to perform periodic power output; and a position detection module, used to determine the periodic drug infusion amount, and when the drug infusion amount reaches a preset threshold, the position detection module and/or the program module provide the actuator with a second driving instruction.

According to one aspect of the present invention, the infusion device further includes an elastic member that applies an elastic force to the driving unit to reset the driving unit.

According to one aspect of the present invention, the infusion device includes two actuators that alternately perform periodic power output.

According to one aspect of the present invention, the actuator is a linear actuator.

According to one aspect of the present invention, the linear actuator is a shape memory alloy or shape memory polymer.

According to one aspect of the present invention, the first driving instruction includes energized time T1 and de-energized time T2, and the de-energized time T2 is not less than the shortest time t required for the linear actuator to recover from deformation.

According to one aspect of the present invention, the second driving instruction includes de-energized time T3, and the de-energized time T3 is not less than the shortest time t required for the linear actuator to recover from deformation.

According to one aspect of the present invention, after the de-energized time T3, the first driving instruction replaces the second driving instruction.

According to one aspect of the present invention, the position detection module includes a position detection element, and the position detection element detects the position through a non-contact detection method.

According to one aspect of the present invention, the position detection element is a magnetic element.

According to one aspect of the present invention, the position detection element is arranged in the piston or the screw or the junction of the screw and the piston.

According to one aspect of the present invention, the position detection element is provided in the piston, and the piston is provided with at least one recess for accommodating the detection element.

According to one aspect of the present invention, the recess is provided with a plurality of projects for fixing the detection element.

According to one aspect of the present invention, the recess also provides a positioning part for further fixing the position detection element.

According to one aspect of the present invention, the infusion device comprises an infusion mechanism module and a control mechanism module, the drug reservoir, the drive wheel, the driving unit, and actuator are provided on the infusion mechanism module, the program module and the position detection module are provided on the control mechanism module.

According to one aspect of the present invention, the infusion mechanism module and the control mechanism module are designed separately, and the control mechanism module can be reused.

According to one aspect of the present invention, the infusion mechanism module and the control mechanism module are disposed of in one housing, discarded together after a single-use.

The invention discloses an artificial pancreas, comprises a highly integrated drug infusion device and a detection mechanism module configured to detect blood glucose continuously, connected or integrated with the control mechanism module and the infusion mechanism module of the infusion device.

According to one aspect of the present invention, any two of the control mechanism module, the infusion mechanism module and the detection mechanism module, are connected or integrated configured to form a single part whose attached position on the skin is different from the third module.

According to one aspect of the present invention, the control mechanism module, the infusion mechanism module, and detection mechanism module are connected or integrally configured to form a single part attached on only one position on the skin.

Compared with the prior art, the technical solution of the present invention has the following advantages:

In the interlocking drug infusion device disclosed by the present invention, the program module provides a first driving instruction for controlling the actuator to perform periodic power output, and the position detection module is used to determine the periodic drug infusion amount, when the drug infusion amount reaches the preset threshold, the position detection module and/or program module provides the actuator with a second driving instruction. The program module and the position detection module physically form a synchronous interlock mechanism to prevent over-infusion in the event of failure of electronic components or preset programs, avoiding the risk of hypoglycemia or even coma.

Furthermore, the program module and the position detection module can form an interlocking mechanism in a variety of ways to ensure that in the event of failure of electronic components or control programs, the infusion will not be overdosed, avoiding the risk of hypoglycemia or coma. For example, when the preset threshold is equal to the normal drug infusion amount of the drug infusion device within T1 time, the position detection module and/or program module control the linear actuator de-energized for T3 time. After that, the second driving instruction is replaced with the first drive instruction, and the linear actuator can normally perform periodic power output according to the preset program. When the preset threshold is greater than the normal drug infusion amount of the drug infusion device within T1 time, the position detection module and/or the program module controls the linear actuator de-energized for T3 time. After that, the second driving instruction is no longer replaced with the first drive instruction. The linear actuator terminates the periodic power output and no more drug infusion.

Furthermore, the de-energized time of each cycle of the linear drive in the first driving instruction of the program module is longer than the shortest time required for the linear drive to recover from deformation. The de-energized time of the linear drive in the second drive instruction is also longer than the shortest time required for the linear drive to recover from deformation, which can ensure that the linear actuator fully recovers to the initial state before the next deformation.

Furthermore, the elastic member applies a restoring force to the driving unit, and the elastic member cooperates with the linear actuator to make the driving unit reciprocate. The elastic member can automatically reset the driving unit without consuming power, reducing the power consumption of the infusion device.

Furthermore, the position detection element can be flexibly arranged at one or more places of the piston, the screw or the junction of the piston and the screw according to the actual layout to optimize the internal design of the infusion mechanism module.

Furthermore, the piston is provided with a recess. The recess is provided with projects and a positioning part for accommodating and fixing the detection element, preventing the detection element from shaking and causing deviation of the sensing information and affecting the detection result.

DETAILED DESCRIPTION

Figure 1A:
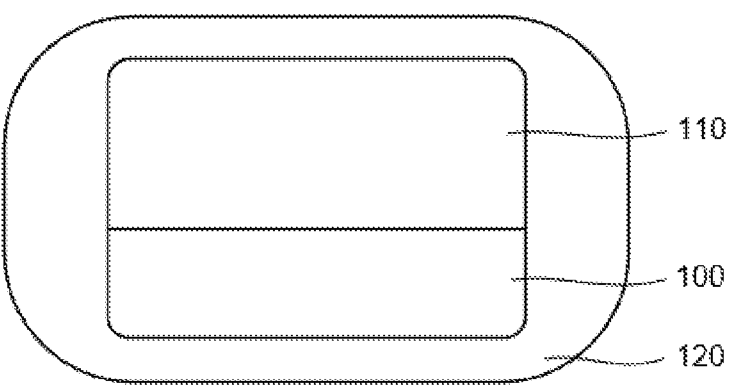
FIG. 1*a* and FIG. 1*b* are schematic top views of the drug infusion device according to two embodiments of the present invention.

As mentioned above, in the prior art, the current drug infusion device uses a control program to control the driving mode of the linear actuator, once the control program or electronic components fail, the drug infusion will be completely out of control, which will result in a potential risk of hypoglycemia and coma.

In order to solve this problem, the present invention provides a drug infusion system. The driving wheel assembly includes a driving wheel body and a movable block; when the movable block is opened, the screw does not engage with the driving wheel assembly, the drug filling can be completed by the thrust generated during the filling process, no need for the assistance of other parts, making the infusion device with a simple arrangement, small size and low cost. When the movable block is closed, the screw engages with the driving wheel assembly, and the screw can only slide under the thrust generated by the rotation of the driving wheel. It cannot slide freely, making the infusion device with good infusion effect and user experience.

Various exemplary embodiments of the present invention will now be described in detail regarding the figures. The relative arrangement of the components and the steps, numerical expressions and numerical values outlined in the embodiments are not construed as limiting the scope of the invention.

In addition, it should be understood that, for ease of description, the dimensions of the various components shown in the figures are not necessarily drawn in the actual scale relationship; for example, the thickness, width, length or distance of certain units may be exaggerated relative to other mechanism modules.

The following description of the exemplary embodiments is merely illustrative and does not limit its application or use to the invention. The techniques, methods, and devices are known to those of ordinary skill in the art and may not be discussed in detail. However, such techniques, methods, and devices should be considered as part of the specification.

It should be noted that similar reference numerals and letters indicate similar items in the following figures. Therefore, once an item is defined or illustrated in a drawing, it will not be discussed further in the following description of the drawings.

Figure 1B:
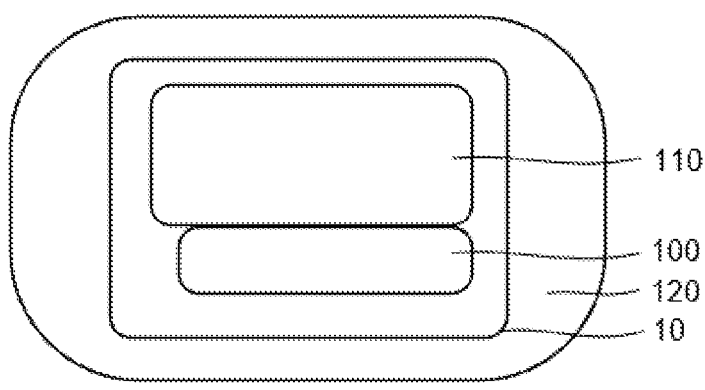

FIG. 1*a* and FIG. 1*b* are schematic top views of the drug infusion device according to two embodiments of the present invention.

In the embodiment of the present invention, the interlocking drug infusion device comprises a control mechanism module 100, an infusion mechanism module 110 and an adhesive patch 120, which will be described separately below. In other embodiments of the present invention, the interlocking drug infusion device may include more parts, which are not specifically limited here.

In the embodiment of the present invention, the infusion mechanism module 110 and the control mechanism module 100 are designed separately and connected by a waterproof plug or directly engaged and electrically connected into a whole. Details regarding how the reliability of the electrical connection has been improved when the infusion mechanism module 110 and the control mechanism module 100 are directly engaged and electrically connected into a whole will be described below. The infusion mechanism module 110 can be reused, and the control mechanism module 100 is discarded after a single use, as shown in FIG. 1*a*. In another embodiment of the present invention, the infusion mechanism module 110 and the control mechanism module 100 are connected by a wire and disposed of inside the same housing 10. Attached to a certain position of the user's skin by the adhesive patch 150, both units will be discarded together after a single use, as shown in FIG. 1*b*.

The interlocking drug infusion device of the embodiment of the present invention includes a control mechanism module 100, which receives signals or information from a remote device or a body fluid parameter detection device (such as CGM), and controls the infusion device to infuse drug(s) accordingly.

Inside the housing 101 of the control mechanism module 100 are disposed of program modules, circuit board(s) and related electronic units for receiving signals or issuing control instructions, as well as other mechanical units or parts necessary for realizing the infusion function, which is not limited herein. In another embodiment of the present invention, a power supply 133 can also be provided in the control mechanism module. Preferably, in the embodiment of the present invention, the power supply 133 is provided in the infusion mechanism module 110, which will be described below.

Figure 2A:
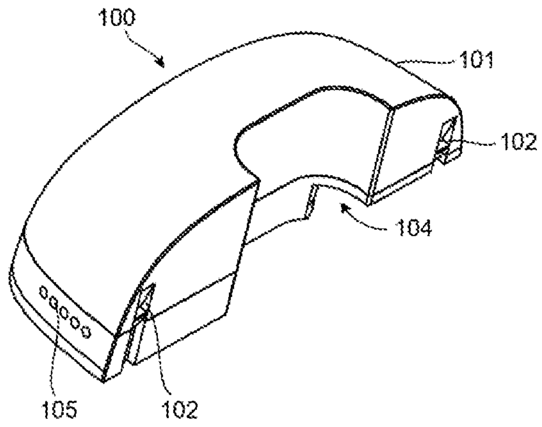
FIG. 2*a* and FIG. 2*b* are schematic views of the control mechanism module according to an embodiment of the present invention.
Figure 2B:
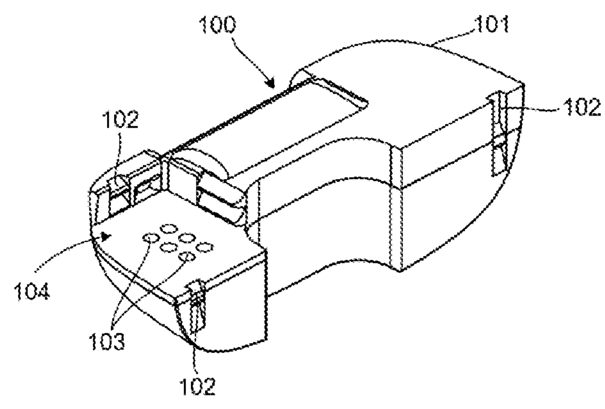

FIG. 2*a* and FIG. 2*b* are schematic views of the control mechanism module according to an embodiment of the present invention.

The control mechanism module 100 further includes the first electrical contact 103 exposed on its surface. The first electrical contact 103 is used as a circuit connection terminal to connect the internal circuits provided in the control mechanism module 100 and the infusion mechanism module 110, respectively. The embodiment of the present invention does not specifically limit the positions of the first electrical contact 103.

Compared with the plug connector used as a connection terminal in the prior arts, the contact area of the electrical contact is much smaller, which provides more flexibility to the mechanism module design, and can effectively reduce the volume of the control mechanism module. At the same time, these smaller electrical contacts can be directly connected to the internal circuit or electrical components. They could also be directly soldered on the circuit board, which helps to optimize the design of the internal circuit and effectively reduce the complexity of the circuit, thereby saving costs and reducing the volume of the infusion system. Furthermore, the electrical contacts are exposed on the surface of the control mechanism module 100 to facilitate electrical connection with connection ends on other mechanism modules. The above technical advantages of the electrical contacts apply to the first electrical contact 103 on the control mechanism module 100 and the second electrical contact 113 on the infusion mechanism module 110, which will not be described in detail below.

The type of the first electrical contact 103 includes rigid metal pins or elastic conductive members. Preferably, in the embodiment of the present invention, the first electrical contact 103 is a rigid metal pin. One end of the first electrical contact 103 is electrically connected to the connection end provided inside the control mechanism module 100. In contrast, the other end is exposed on the surface of the lower housing 101*b*. The rest part of the first electrical contact 103 is tightly embedded in the housing 101, thus keeping the internal control mechanism module 100 isolated from the outside.

The elastic conductive member includes conductive spring, conductive silica gel, conductive rubber, or conductive leaf spring. One end of the elastic conductive member is used to electrically connect with the internal connection end in the control mechanism module 100, while the other end is used to connect with other connection ends electrically.

As in an embodiment of the present invention, the first electrical contact 103 is a conductive spring. When the electrical contacts are in contact with each other, the elasticity of the conductive spring can enhance the reliability of the electrical connection. Similar to the rigid metal pin, one end of the conductive spring is exposed on the surface of the lower housing 101*b*. In contrast, the remaining part of the conductive spring is tightly embedded in the housing 101 and electrically connected with internal circuits or electrical components. The connection end disposed inside the control mechanism module 100 can be a conductive lead, a specific part of a circuit, or an electrical element.

It should be noted that the "tightly embedded" in the embodiment of the present invention suggests that there is no gap between the electrical contact and the housing 101, keeping the control mechanism module 100 tightly sealed. The following "tightly embedded" has the same meaning as here.

In another embodiment of the present invention, the first electrical contact 103 is a conductive spring, but it is not tightly embedded in the housing 101. Instead, a sealing element is provided in a groove, both of which are disposed around the area where the first electrical contacts 103 are located, thus sealing the electrical contact area and the control mechanism module 100.

In the embodiment of the present invention, the control mechanism module 100 is further provided with the first engaging portions 102, which is used to fasten the second engaging portion 112 disposed on the infusion mechanism module 110 to assemble the control mechanism module 100 infusion mechanism module 110. Details regarding how the mechanism works to enable the electrical connection between the first electrical contacts 103 and the second electrical contacts 113 will be described below.

The first engaging portion 102 and the second engaging portion 112 include one or more hooks, blocks, holes, and slots that can be engaged with each other. The positions of the hooks, blocks, holes, and slots can be flexibly adjusted, according to the shape and mechanism module features of the control mechanism module 100 and the infusion mechanism module 110, such as disposed in the interior or on the surface of the corresponding mechanism module, which is not specifically limited herein.

In the embodiment of the present invention, the control mechanism module 100 is further provided with a concave 104 that fits the convex portion 114 disposed at the bottom of the case of the infusion mechanism module 110, which will be described in detail below. Preferably, the first electrical contacts 103 are provided in the concave 104, as shown in FIG. 2*b*.

In the embodiment of the present invention, a buzzer (not shown) is also provided in the control mechanism module 100. When the infusion process starts or ends, the infusion device malfunctions, the drug is exhausted, the control mechanism module 100 issues an error command or receives an error message, etc., the buzzer is used to issue alarm signals, such as sound or vibration, notifying the user to adjust or replace the device in time.

Preferably, in the embodiment of the present invention, the housing 101 of the control mechanism module 100 is provided with a sound-permeable outlet 105 to allow the sound alarm signal from the buzzer to be sent out. In order to achieve a good sealing effect and ensure the normal operation of the buzzer, a waterproof sound-permeable membrane (not shown) is disposed between the sound-permeable outlet 105 and the buzzer. Therefore, the waterproof sound-permeable membrane needs to have a certain porosity to ensure the sound transmission but prevent water molecules penetration.

Compared with the traditional technical solution in which the buzzer is entirely enclosed in the control mechanism module 100, because of the sound-permeable outlet 105, a less loud sound signal emitted from the buzzer would be enough to raise the user's attention, which reduces the energy consumption of the buzzer, thereby optimizing the power consumption configuration of the infusion device and saving production costs.

Figure 3A:
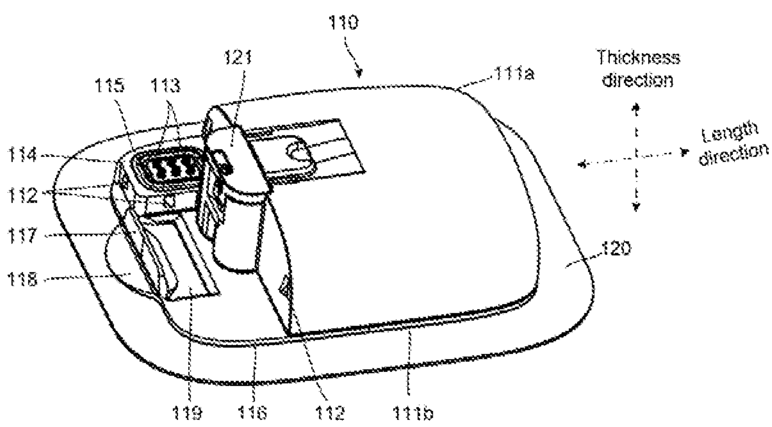
FIG. 3*a* is a schematic view of the infusion mechanism module according to an embodiment of the present invention.
Figure 3B:
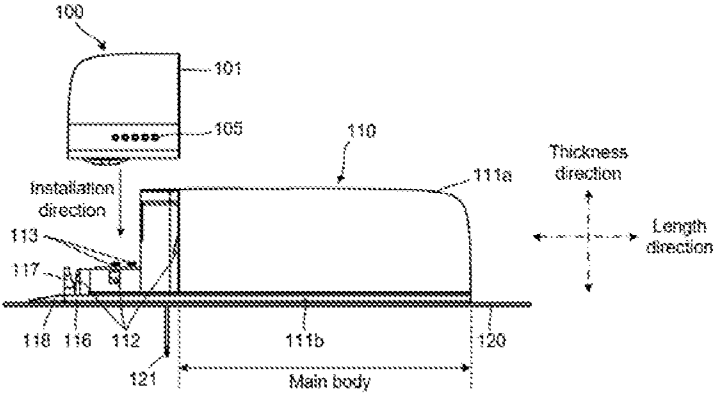
FIG. 3*b* is a side view of the assembly of the control mechanism module and the infusion mechanism module according to an embodiment of the present invention.
Figure 3C:
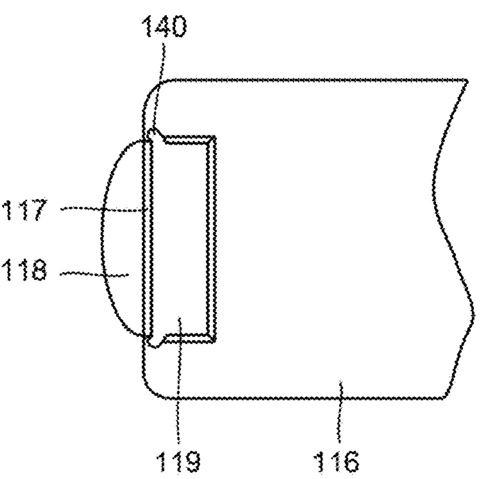
FIG. 3*c* is a schematic top view of the lower case of the infusion mechanism module according to an embodiment of the present invention.
Figure 3D:
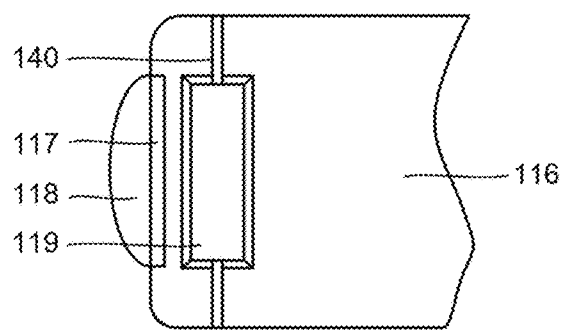
FIG. 3*d* is a schematic top view of the lower case of the infusion mechanism module according to another embodiment of the present invention.

FIG. 3*a* is a schematic view of the infusion mechanism module 110 according to the embodiment of the present invention. FIG. 3*b* is a side view of the assembly of the control mechanism module 100 and the infusion mechanism module 110 according to the embodiment of the present invention. FIG. 3*c* is a schematic top view of the lower case of the infusion mechanism module according to an embodiment of the present invention. FIG. 3*d* is a schematic top view of the lower case of the infusion mechanism module according to another embodiment of the present invention.

The interlocking drug infusion device further includes an infusion mechanism module 110 with a case. A mechanical module, an electric control module, and other auxiliary modules for completing the drug infusion process are provided inside the case, which will be described in detail below. The case of the infusion mechanism module 110 may include multiple parts. As in the embodiment of the present invention, the case of the infusion system includes an upper case 111*a* and a lower case 111*b*.

As mentioned above, in the embodiment of the present invention, the infusion mechanism module 110 is provided with the second engaging portions 112, which is used to engaged and fasten the corresponding first engaging portions 102. The positions where the first engaging portions 102 and the second engaging portions 112 are provided correspondingly.

In the embodiment of the present invention, the infusion mechanism module 110 is provided with second electrical contacts 113, which are used to press against the corresponding first electrical contacts 103 to create an electrical connection between the control mechanism module 100 and the infusion mechanism module 110. The compression between these two corresponding electrical contacts disposed on different parts can improve the reliability of the electrical connection. Similar to the first electrical contacts 103, one of the second electrical contact 113 also includes a rigid metal pin and an elastic conductive member. Preferably, in the embodiment of the present invention, the second electrical contact 113 is a conductive spring. Similarly, the conductive spring can improve the electrical connection performance. A groove is also arranged around the area where the second electrical contact 113 is disposed, and a sealing member 115 is arranged in the groove. Similarly, the elasticity of the conductive spring can further improve the electrical connection performance.

Preferably, in the embodiment of the present invention, the two ends of the conductive spring have different diameters. And the diameter of the end exposed to the outside of the infusion mechanism module 110 is shorter than that of the end inside the infusion mechanism module 110.

In this way, the conductive spring can be held in the case because of the longer diameter; Thus, when the control mechanism module 100 is not installed on the infusion mechanism module 110, the longer diameter of the inner end can prevent the conductive spring from detaching from the infusion mechanism module 110.

The embodiment of the present invention does not limit the position at where second electrical contacts 113 are arranged, as long as it can be electrically connected to the corresponding first electrical contacts 103. Preferably, in the embodiment of the present invention, the upper case 111*a* of the infusion mechanism module 110 includes a convex portion 114 where the second electrical contacts 113 are disposed, as shown in FIG. 3*a*. The shape of the convex portion 114 corresponds to that of the concave 104 disposed on the control mechanism module 100, allowing the two portions to tightly fit each other and press the first electrical contacts 103 and the corresponding second electrical contacts 113 against each other to realize the electrical connection.

In other embodiments of the present invention, the convex portion 114 may be provided on the lower case 111*b*. When the infusion mechanism module 110 includes an integral case, the convex portion 114 will be a part of the integral case not specifically limited herein.

The method of assembling the control mechanism module 100 and the infusion mechanism module 110 to each other includes pressing the control mechanism module 100 on the infusion mechanism module 110 along the thickness direction of the infusion mechanism module 110, thereby engaging the first engaging portion 102 and the second engaging portion 112; or pressing the control mechanism module 100 on the infusion mechanism module 110 along the length direction of the infusion mechanism module 110. Alternatively, the control mechanism module 100 can be pressed along with any angle between the thickness direction and the length direction of the infusion mechanism module 110, making the first engaging portion 102 and the second engaging portion 112 engaged with each other. Preferably, in the implementation of the present invention, the method by which the control mechanism module 100 and the infusion mechanism module 110 are assembled is to press the control mechanism module 100 on the infusion mechanism module 110 along with the thickness direction of the infusion mechanism module 110, making the first engaging portion 102 and the second engaging portion 112 engaged with each other, as shown the installation direction in FIG. 3*b*.

In the embodiment of the present invention, the lower case 111*b* of the infusion mechanism module 110 further includes an outward extending portion 116. A block 117 is provided outside the outer extending portion 116, as shown in FIG. 3*a*. As mentioned above, the control mechanism module 100 is pressed to the engaging position along the thickness direction of the infusion mechanism module 110; thus, block 117 can prevent the control mechanism module 100 from detaching along the length direction of the infusion mechanism module 110, ensuring the normal operation of the infusion system. Obviously, in another embodiment of the present invention, if the control mechanism module 100 is pressed to the engaging position along with other directions, the control mechanism module 100 can also be prevented from detaching from the infusion mechanism module 110 by adjusting the position of the block 117.

It should be noted here that "outer" and "outside" are relative to the main body of the infusion mechanism module 110, where they belong to a concept of the relative position, as shown in FIG. 3*a* or FIG. 3*b*. The "outside" below have the same meaning as here.

In the embodiment of the present invention, the outer end of the outer extending portion 116 is also provided with a pressing portion 118 for releasing the blocking effect of block 117. While the user is replacing the infusion mechanism module 110, the control mechanism module 100 can be released from block 117 by pressing the pressing portion 118 with a finger. Then, the user can remove the control mechanism module 100 from the infusion mechanism module 110 with two fingers.

Another embodiment of the present invention can also be provided with an unlocking hole 119 disposed of in the inner side of block 117. While the pressing portion 118 is pressed, a finger can enter the unlocking hole 119, thereby pushing the control mechanism module 100 out to separate the control mechanism module 100 from the infusion mechanism module 110. In the embodiment of the present invention, the unlocking hole 119 is square. The square unlocking hole 119 can facilitate the smooth entry of fingers. In other embodiments of the present invention, the unlocking hole 119 may also have other shapes, which is not specifically limited here.

The lower case 1*l*1*b* of the infusion mechanism module 110 is also provided with one or more crease grooves 140. Two crease grooves 140 are provided on both sides of the unlocking hole 119, as shown in FIG. 3*c* and FIG. 3*d*. After the crease groove, 140 is provided, the thickness or width of the lower case 111*b* at the crease groove 140 (as shown by the arrows in FIG. 3*c* and FIG. 3*d*) is reduced. When the user presses the pressing portion 118, the lower case 111*b* is easily broken at the crease groove 140, and the blocking of the control mechanism module 100 by block 117 is more smoothly released.

Preferably, in the embodiment of the present invention, two crease grooves 140 are provided at the both ends of block 117, respectively, as shown in FIG. 3*c*. In another embodiment of the present invention, the crease groove 140 is provided on two corresponding lateral sides of the unlocking hole 119, as shown in FIG. 3*d*.

The interlocking drug infusion device further includes a needle unit 121, used for infusing the drug to the subcutaneous tissue.

An adhesive patch 120 is also provided on the bottom of the lower case 111*b* to attach the infusion device to the user's skin surface.

Figure 4A:
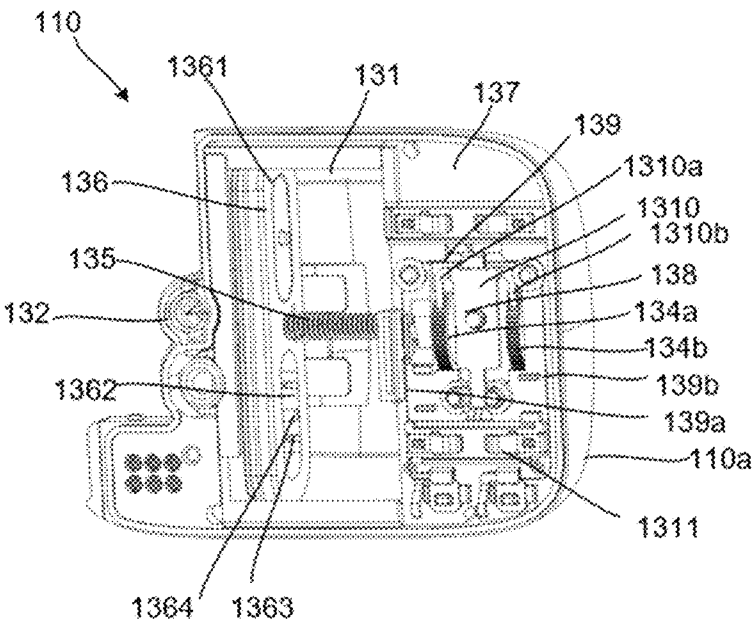
FIG. 4*a* is a schematic view of the infusion mechanism module according to an embodiment of the present invention.
Figure 4B:
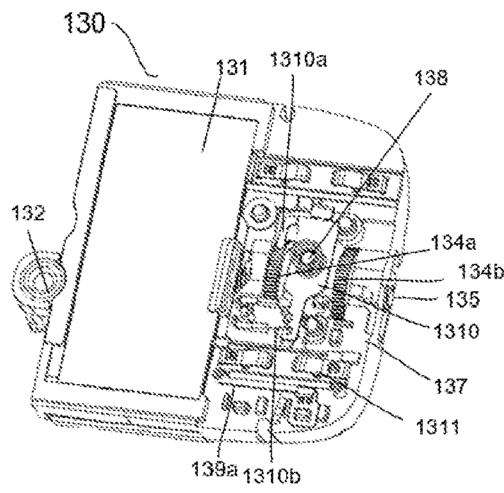
FIG. 4*b* is schematic view of the internal mechanism module of the infusion mechanism module according to an embodiment of the present invention.
Figure 4C:
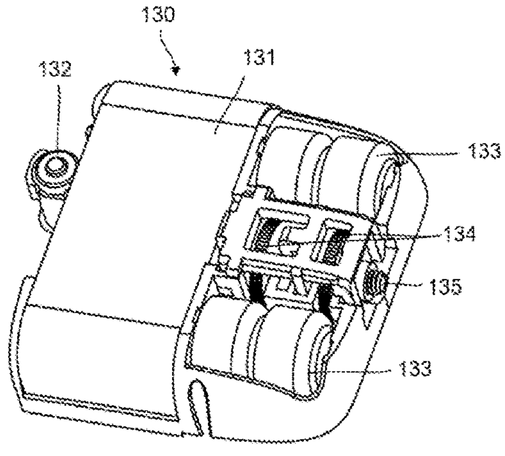
FIG. 4*c* is a schematic view of the internal mechanism module of the infusion mechanism module from another perspective according to another embodiment of the present invention.

FIG. 4*a* is a schematic view of the infusion mechanism module 110 of the embodiment of the present invention. FIG. 4*b* is a schematic view of the internal mechanism module 130 of the infusion mechanism module 110 of another embodiment of the present invention. FIG. 4*c* is a schematic view of the internal mechanism module of the infusion mechanism module from another perspective of another embodiment of the present invention.

In the embodiment of the present invention, the internal mechanism module 130 includes mechanical units and electronic control units that are used to realize the infusion function, such as a drug reservoir 131, a drug outlet 132, a power supply 133, a driving wheel 134, a screw 135, a piston 136, a driving unit 1310 and a frame 137 for carrying the mentioned parts, etc. The drug storage cartridge 131 is used for containing drugs, including but not limited to insulin, glucagon, antibiotics, nutrient solution, analgesics, anticoagulants, gene therapy drugs, cardiovascular drugs or chemotherapy drugs. The piston 136 and the screw 135 are arranged in the drug reservoir 131, and the piston 136 is used to infuse the drug into the body. The screw 135 is connected with the piston 136, to push the piston 136 to move forward, so as to achieve drug infusion. The screw 135 is a rigid screw or a flexible screw.

In an embodiment of the present invention, the driving unit 1310 includes two driving arms 1310*a* and 1310*b*. As shown in FIG. 4*a*, the driving wheels 134*a* and 134*b* are provided with teeth, and both driving arms 1310*a* and 1310*b* can push the teeth to forward. The frame 137 is provided with a rotating shaft 138, and a power unit 139 is electrically connected to the driving unit 1310. The power unit 139 includes the power components 139*a* and 139*b*. When the program module in the control mechanism module 100 controls the power component 139*b* to rotate clockwise around the rotating shaft 138, the driving arm 1310*a* pushes the teeth of the driving wheel 134*a* forward. At that time, the driving wheels 134*a* and 134*b* rotate synchronously and drive the screw 135 forward. Thereby the infusion device performs drug infusion. At the same time, the driving arm 1310*b* slides on the surface of the driving wheel 134*b* to complete the reset.

When the program module in the control mechanism 100 controls the power component 139*a* to rotate counterclockwise around the rotating shaft 138, the driving arm 1310*b* of the driving unit 1310 pushes the teeth of the driving wheel 134*b* forward. At that time, the driving wheels 134*a* and 134*b* rotate synchronously; thereby the infusion device performs drug infusion. At the same time, the driving arm 1310*a* slides on the surface of the driving arm 134*a* to complete the reset.

In the embodiment of the present invention, the power components 139*a* and 139*b* are actuators. The actuators include electrically driven linear actuators or electrically heated linear actuators. The actuators are shape memory alloys or shape memory polymers. After being energized, the physical form of the linear actuator's material changes, making it shrinkage deformation, thereby outputting driving power to pivot the driving unit 1310. The higher the current is, within a limited time, the larger shrinkage deformation is, and the greater the driving power outputs. Obviously, when the current is constant, the driving power output by the linear actuator is constant within a limited time.

After the power component 139*a* or 139*b* finishes a driving within the time T1, the program module controls the power component 139*a* or 139*b* de-energized for the time T2 to recover from the deformed state to the initial state. Therefore, in the embodiment of the present invention, the first driving instruction for controlling the power component 139*a* or 139*b* to perform periodic power output is preset in the program module. The first driving instruction controls the power component 139*a* or 139*b* energized for T1 time at a predetermined current or voltage, then de-energized for T2 time. It is periodically energized or de-energized. The de-energized time T2 is not less than the shortest time t for the linear actuator to recover from deformation to ensure that the linear actuator can be completely recovered to the initial state and avoid any inaccurate infusions.

Obviously, when the power component 139*a* is deformed within the energized time T1, the power component 139*b* is within the de-energized time T2. On the contrary, when the power member 139*b* is deformed within the energized T1, the power member 139*a* is within the de-energized time T2. That is, in the embodiment of the present invention, in the first driving instruction of the program module, the power components 139*a* and 139*b* are alternately energized and de-energized, the energized time of the power component 139*a* is the de-energized time of the power component 139*b*, and the de-energized time of the power component 139*a* is energized time of the power component 139*b*. In order to ensure that the linear actuator can fully recover to the initial state within the de-energized time T2, the energized time T1 and de-energized time T2 of the power components 139*a* and 139*b* are both not less than the shortest time t required for the linear actuator to recover deformation. In the embodiment of the present invention, the relationship between the energized time T1 and the de-energized time T2 is not limited. For example, in an embodiment of the present invention, in order to achieve smooth infusion of the infusion device, when the voltage or current applied on the power components 139*a* and 139*b* are constant and equal, the energized time of the power components 139*a* and 139*b* is equal; in another embodiment of the present invention, when the voltage or current applied on the power components 139*a* and 139*b* is constant but not equal, smooth infusion can also be achieved by adjusting the energized time of the power components 139*a* and 139*b*.

The power components 139*a* and 139*b* can be composed of a continuous shape memory alloy or shape memory polymer, or it can be composed of two pieces of shape memory alloy or shape memory polymer, with no specific limitation here, as long as when the force is applied, the driving unit 1310 can be rotated.

In another embodiment of the present invention, the driving unit 1310 includes only one driving arm 1310*a*. As shown in FIG. 4*b*, when the first driving instruction in the program module controls the power component 139*a* to rotate counterclockwise around the rotating shaft 138, the driving arm 1310*a* pushes the teeth of the driving wheel 134*a* forward. At that time, the driving wheels 134*a* and 134*b* rotate synchronously drive the screw 135 forward; thereby the infusion device performs drug infusion. In the embodiment of the present invention, the power component 139*a* is a linear actuator; specifically, it is a shape memory alloy or a shape memory polymer, and the power member 139*b* is an elastic member. The elastic member generates a gradually increasing elastic force. When the program module controls the power component 139*a* energized for the time T1 and then de-energized for time T2, the power component 139*a* stops providing power; the driving arm 1310*a* of the driving unit 1310 rotates clockwise around the rotating shaft 138 under the elastic force of the power component 139*b*; the driving arm 1310*a* stop pushing the teeth of the driving wheel 134*a*, so that the driving wheels 134*a* and 134*b* stop rotating, and the screw 135 stops marching, thereby the infusion device does not perform drug infusion. At the same time, the driving end 1310*a* slides on the teeth surface of the driving wheel 134*a* to reset until the driving unit 1310 stops rotating. In the embodiment of the present invention, the types of elastic components include, but are not limited to, compression springs, extension springs, torsion springs, elastic sheets, elastic plates, elastic rods, elastic rubbers, and the like. The elastic component can automatically spring back the drive unit 1310 to its original position without external force. It does not need to consume electric energy, thereby reducing the power consumption of the infusion device. Specifically, in the embodiment of the present invention, the elastic member 139*b* is a torsion spring. The torsion spring is more conducive to the return of the driving unit 1310.

Similarly, in the embodiment of the present invention, the first driving instruction for controlling the power component 139*a* to perform periodic power output is provided in the program module. The first driving instruction is controlling the power component 139*a* energized for T1 time at a predetermined current or voltage, then de-energized for T2 time. It is periodically energized or de-energized. The de-energized time T2 is not less than the shortest time t for the linear actuator to recover from deformation to ensure that the linear actuator can be completely recovered to the initial state and avoid inaccurate infusion.

In order to prevent the linear actuator from being energized for a long time due to the failure of electronic components or control programs, that is, the linear actuator is in a deformed state for a long time. On the one hand, overdose caused by the amount of deformation of the linear actuator exceeds the predetermined length, will result in the risk of hypoglycemia or even coma. On the other hand, permanent deformation of the linear actuator caused by the amount of deformation exceeding the limit deformation amount that the linear actuator can withstand will make the infusion device completely useless. In the embodiment of the present invention, a position detection module is further provided in the infusion device. The position detection module is operably connected to the control mechanism module for periodically determining the amount of drug infusion. The position detection module includes a detection circuit (not shown) and at least one position detection element 1361. The detection circuit is arranged in the control mechanism module, and the position detection element 1361 is arranged in the infusion mechanism module 110. The detection circuit cooperates with at least one detection element 1361 to provide corresponding signals, data or information that need to be analyzed and processed to determine the amount of drug infusion. The position detection module and/or the program module provide the linear actuator with a second driving instruction when the drug infusion amount reaches the preset threshold in one cycle. The second driving instruction is controlling the linear actuator de-energized for T3 time. It should be noted that when the drug infusion amount in one cycle reaches the preset threshold, the position detection module and/or the program module provide the linear actuator with a second driving instruction, which means that when the drug infusion volume in one cycle reaches the preset threshold, the position detection module or the program module may provide the second driving instruction for the linear actuator independently, or the position detection module and the program module may jointly provide the second driving instruction for the linear actuator.

For example, in one embodiment of the present invention, the preset threshold is equal to the normal drug infusion amount of the drug infusion device within T1 time. When the drug infusion amount in one cycle detected by the position detection module reaches the preset threshold, the position detection module provides the second driving instruction. The second driving instruction controls the linear actuator de-energized for T3 time. After that, the second driving instruction is replaced with the first driving instruction. The linear actuator can normally perform periodic power output according to the preset program, preventing overdose in advance and avoiding hypoglycemia and coma. In another embodiment of the present invention, when the drug infusion amount in one cycle detected by the position detection module reaches the preset threshold, the program module provides a second driving instruction. It controls the linear actuator de-energized for T3 time. In yet another embodiment of the present invention, when the drug infusion amount in one cycle detected by the position detection module reaches the preset threshold, the position detection module and the program module jointly provide a second driving instruction and control the linear actuator de-energized for T3 time.

In another embodiment of the present invention, the preset threshold is greater than the normal drug infusion amount of the drug infusion device within T1 time. When the drug infusion amount in one cycle is detected by the position detection module, reaching the preset threshold, the position detection module and/or the program module will provide the second driving instruction and control the linear actuator de-energized for T3 time. After that, the second driving instruction is no longer replaced with the first drive instruction. The linear actuator terminates the periodic power output and no more drug infusion, which can prevent overdose and avoid hypoglycemia and coma. Here, the meaning of the position detection module and/or the program module provides the second driving instruction is the same as described above, which will not be repeated here.

It should be noted that the de-energized time T3 is not less than the shortest time t required for the linear actuator to recover from deformation, so as to ensure that the linear actuator can fully recover to the initial state before the next deformation state.

In the embodiment of the present invention, the position detection element 1361 is arranged in the piston 136. In other embodiments of the present invention, the detection element 1361 may also be arranged in other components of the infusion mechanism module 110, such as one or more places of the screw 135, the junction between the screw 135 and the piston 136, etc., which are not limited here. It can be flexibly set according to the actual layout to optimize the internal design of the infusion mechanism module. During the drug infusion, the position detection element 1361 detects the position changes of the end of the piston 136 or the screw 135 in the reservoir 317 along the axial direction (the moving direction of the screw 135), the detection circuit converts the axial position information of the piston 136 or the end of the screw 135 into drug infusion amount. The position detection module receives the information of the drug infusion amount. When the drug infusion amount information is equal to a preset threshold, the program module and/or the position detection module controls the linear actuator de-energized for T3 time.

Preferably, in the embodiment of the present invention, the position detection element 1361 detects the position of the end of the piston 136 or the screw 135 by a non-contact detection method. The position detection element 1361 is a magnetic element for providing a magnetic field. The detection circuit is provided with a magnetic sensor. The magnetic field intensity of the magnetic element induced will be changed with the change of the position of the magnetic element, that is, the end of the piston 136 or the screw 135. Therefore, the detection circuit can calculate the position change of the piston 136 end or the screw 135 through the change of the induced magnetic field, and further converted into the information of the drug infusion amount.

Preferably, in the embodiment of the present invention, the position detection element 1361 is provided in the piston 136, and the piston 136 is provided with at least one recess 1362 for accommodating the detection element 1361. The recess 1362 is also provided with a plurality of projects 1363, for fixing the detection element 1361. A positioning portion 1364 is further provided in the middle of the recess 1362 to fix the detection element 1361 further, and prevent deviation of the sensing information of the detection element 1361 from shaking, affecting the detection result.

In the embodiment of the present invention, the power supply 133 is a conventional button battery. In other embodiments of the present invention, the power supply 133 may also be other types of batteries, as long as it can meet the requirements for supplying power to the infusion system. Preferably, in the embodiment of this present invention, the type of the power supply 133 is a double-row battery pack; that is, two rows of button batteries are arranged on both sides of the driving wheel 134, respectively, as shown in FIG. 4*c*. Conventionally, the discharge capacity of button batteries is low. The double-row button battery pack can reduce the discharge level of each battery, thereby extending the service life of the battery. Furthermore, the double-row design of the power supply 133 can make the full use of the internal space and improve the integration within the internal mechanism module in the infusion system.

The infusion mechanism module 110 in the embodiment of the present invention is also provided with a circuit board or multiple three-dimensional circuits coated on the surface of a part of the mechanism module for supplying power to specific structural units. According to the internal arrangement characteristics of the infusion device, the shape and position of the three-dimensional circuit can be flexibly designed, which can make the full use of the internal space of the infusion mechanism module, making the arrangement more compact. The circuit board is a hard/rigid circuit board or a flexible circuit board. Preferably, in the embodiment of the present invention, the circuit board is flexible. The shape of the flexible circuit board is adjustable, allowing it to be flexibly designed according to the internal space of the infusion mechanism module 110. At the same time, multiple connection ends can be provided on the flexible circuit board to be electrically connected to second electrical contacts 113, thereby connecting the circuits of the control mechanism module 100 and the infusion mechanism module 110, allowing the infusion system to perform drug infusion function.

An elastic conductor 1311 is also provided inside the infusion mechanism module 130. The elastic conductor 1311 is electrically connected to the power supply 133, and the specific connection end on the circuit board (or three-dimensional circuit), thereby supplying power to specific units. The elastic conductor 1311 are provided with protrusions, which can enhance the electrical connection stability between the elastic conductors and the power supply, the circuit board or specific connection ends on the three-dimensional circuit, and improve the reliability of the electrical connection.

Figure 5:
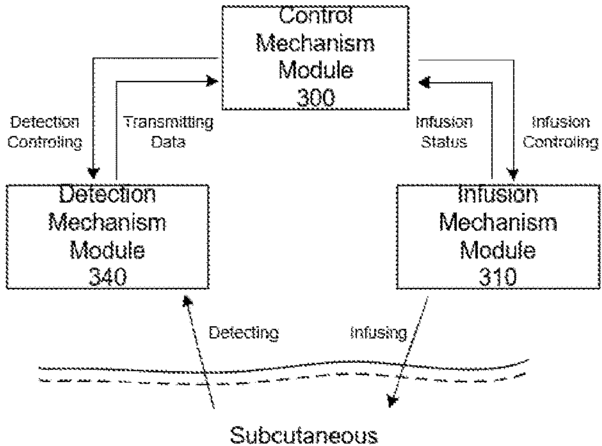
FIG. 5 is a schematic view of the module relationship of the artificial pancreas according to one embodiment of the present invention.

FIG. 5 is a schematic view of the module relationship of the artificial pancreas according to one embodiment of the present invention.

The artificial pancreas disclosed in the embodiment of the present invention comprises the above mentioned infusion device with integrated power supply; and a detection mechanism module 340, connected or integrated with the control mechanism module and infusion mechanism module of the infusion device, configured to detect blood glucose continuously. In one embodiment of the present invention, the detection mechanism module 340 is a Continuous Glucose Monitoring (CGM) for detecting real-time BG, monitoring BG changes, and also sending them to the control mechanism module 300.

The control mechanism module 300 is used to control the detection mechanism module 340 and the infusion mechanism module 310. Specifically, the control mechanism module 300 can receive the blood glucose parameter signal sent by the detection mechanism module 340, and is used to control the detection process of the detection mechanism module 340 and record the infusion information and working status of the infusion mechanism module 310. For example, when the blood glucose information detected by the detection mechanism module 340 after the end of life is inaccurate, the control mechanism module 300 may issue a detection stop instruction to the detection mechanism module 340. For another example, when insulin blockage occurs in the infusion mechanism module 310, the control mechanism module 300 can record the blockage status in time and provide feedback to the patient to eliminate potential safety hazards. Therefore, the control mechanism module 300 is connected to the detection mechanism module 340 and the infusion mechanism module 310, respectively. Here, the connection refers to a conventional electrical connection or a wireless connection.

The infusion mechanism module 310 includes the essential mechanical parts used to infuse insulin and controlled by the control mechanism module 300. According to the current insulin infusion dose calculated by the control mechanism module 300, the infusion mechanism module 310 injects the currently insulin dose required into the user's body. At the same time, the real-time infusion status of the infusion mechanism module 310 can also be fed back to the control mechanism module 300.

The embodiment of the present invention does not limit the specific positions and connection or integration relationships of the detection mechanism module 340, the control mechanism module 300 and the infusion mechanism module 310, as long as the aforementioned functional conditions can be satisfied.

As in an embodiment of the present invention, the control mechanism module 300 and the infusion mechanism module 310 are electrically connected or integrated with each other to form a single part while the detection mechanism module 340 is separately provided in another part. At this time, the detection mechanism module 340 and the control mechanism module 300 transmit wireless signals to each other to realize mutual connection. Therefore, the control mechanism module 300 and the infusion mechanism module 310 can be attached on the same position of the user's skin while the detection mechanism module 340 is attached on the other position.

As in another embodiment of the present invention, the control mechanism module 300 and the detection mechanism module 340 are electrically connected or integrated with each other forming a single part while the infusion mechanism module 310 is separately provided in another part. The infusion mechanism module 310 and the control mechanism module 300 transmit wireless signals to each other to realize mutual connection. Therefore, the control mechanism module 300 and the detection mechanism module 340 can be attached on the same position of the user's skin while the infusion mechanism module 310 is attached on the other position.

As in another embodiment of the present invention, the infusion mechanism module 310 and the detection mechanism module 340 are electrically connected or integrated with each other forming a single part while the control mechanism module 300 is separately provided in another part. The infusion mechanism module 310, the detection mechanism module 340 and the control mechanism module 300 transmit wireless signals to each other to realize mutual connection. Therefore, the infusion mechanism module 300 and the detection mechanism module 340 can be attached on the same position of the user's skin while the control mechanism module 300 is attached on the other position or independent of the user's skin, that is, it is not pasted on any part of the user's skin.

As in an embodiment of the present invention, the three are electrically connected or integrated with each other forming a single part. Therefore, the three modules can be attached together on only one position of the user's skin. If the three modules are attached in the only one position, the number of the device on the user skin will be reduced, thereby reducing the interference of more attached devices on user activities. At the same time, it also effectively solves the problem of the poor wireless communication between separating devices, further enhancing the user experience.

As in another embodiment of the present invention, the three are respectively provided in different mechanism modules, thus being attached on different position. At this time, the control mechanism module 300, the detection mechanism module 340 and the infusion mechanism module 310 respectively transmit wireless signals to each other to realize mutual connection.

It should be noted that the control mechanism module 300 of the embodiment of the present invention also has functions such as storage, recording, and access to the database, thus, the control mechanism module 300 can be reused. In this way, not only can the user's physical condition data be stored, but also the production cost and the user's consumption cost can be saved. As described above, when the service life of the detection mechanism module 340 or the infusion mechanism module 310 expires, the control mechanism module 300 can be separated from the detection mechanism module 340, the infusion mechanism module 310, or both the detection mechanism module 340 and the infusion mechanism module 310.

Generally, the service lives of the detection mechanism module 340, the control mechanism module 300 and the infusion mechanism module 310 are different. Therefore, when the three are electrically connected to each other to form a single device, the three can also be separated from each other in pairs. For example, if one module expires firstly, the user can only replace this module and keep the other two modules continuous using.

Here, it should be noted that the control mechanism module 300 of the embodiment of the present invention may also include multiple sub-modules. According to the functions of the sub-modules, different sub-modules can be respectively assembled in different mechanism module, which is not specific limitation herein, as long as the control conditions of the control mechanism module 300 can be satisfied.

As a summary, the present invention discloses an interlocking drug infusion device nd the artificial pancreas thereof, the infusion mechanism module includes an upper case, a lower case, and a frame, the multiple engaging portions on the upper case and the lower case engaged with the engaging portion on the frame, realizing the stable engaging of the infusion mechanism, improving the stability of the infusion mechanism module; a circuit is provided on the lower case, electrically connected with the electrical connection terminals of the special components on the frame, realizing the internal conduction of the infusion mechanism module, improving the internal electrical connection stability and connection reliability of the infusion mechanism module. The internal space of the infusion mechanism modules is fully used, making the infusion device with high integration, small volume and good user experience.

While the invention has been described in detail regarding the specific embodiments of the present invention, it should be understood that it will be appreciated by those skilled in the art that the above embodiments may be modified without departing from the scope and spirit of the invention. The appended claims define the scope of the invention.

The invention claimed is:

1. An interlocking drug infusion device, comprising:

a drug reservoir, used for accommodating a drug to be infused, provided with a piston and a screw;

a driving wheel, connected with the screw, driving the screw to push the piston forward by rotation;

a driving unit, the driving unit moved in a driving direction to drive the driving wheel to rotate;

at least one actuator, electrically connected to the driving unit, used to provide power for the driving unit in the driving direction after energized;

a program module, electrically connected to the at least one actuator, the program module providing a first driving instruction for controlling the at least one actuator to perform periodic power output; and a position detection module, used to determine a periodic drug infusion amount, wherein when the periodic drug infusion amount reaches a preset threshold, the position detection module and/or the program module provide the at least one actuator with a second driving instruction, wherein the first driving instruction includes energized time T1 and de-energized time T2, and the de-energized time T2 is not less than a shortest time t required for the linear actuator to recover from deformation, the second driving instruction includes de-energized time T3, and the de-energized time T3 is not less than a shortest time t required for the linear actuator to recover from deformation.

2. The interlocking drug infusion device of claim 1, further comprising an elastic member that applies an elastic force to the driving unit to reset the driving unit.

3. The interlocking drug infusion device of claim 1, wherein the at least one actuator comprises two actuators that alternately perform the periodic power output.

4. The interlocking drug infusion device of claim 3, wherein each of the two actuators is a linear actuator.

5. The interlocking drug infusion device of claim 4, wherein the linear actuator is a shape memory alloy or shape memory polymer.

6. The interlocking drug infusion device of claim 1, wherein after the de-energized time T3, the first driving instruction replaces the second driving instruction.

7. The interlocking drug infusion device of claim 1, wherein after the de-energized time T3, the first driving instruction does not replace the second driving instruction.

8. The interlocking drug infusion device of claim 1, wherein the position detection module includes a position detection element, and the position detection element detects a position through a non-contact detection.

9. The interlocking drug infusion device of claim8, wherein the position detection element is a magnetic element.

10. The interlocking drug infusion device of claim 9, wherein the position detection element is arranged in the piston or the screw or a junction of the screw and the piston.

11. The interlocking drug infusion device of claim 10, wherein the position detection element is provided in the piston, and the piston is provided with at least one recess for accommodating the position detection element.

12. The interlocking drug infusion device of claim 11, wherein the recess is provided with a plurality of projects, for fixing the position detection element.

13. The interlocking drug infusion device of claim 12, wherein the recess also provides a positioning part for further fixing the position detection element.

14. The interlocking drug infusion device of claim 1, further comprising an infusion mechanism module and a control mechanism module, the drug reservoir, the drive wheel, the driving unit, and the actuator are provided on the infusion mechanism module, the program module and the position detection module are provided on the control mechanism module.

15. The interlocking drug infusion device of claim 14, wherein the infusion mechanism module and the control mechanism module are detachable to each other, and the control mechanism module is reusable.

16. The interlocking drug infusion device of claim 14, wherein the infusion mechanism module and the control mechanism module are disposed in one housing, discarded together after a single-use.

17. An artificial pancreas, comprising:

the interlocking drug infusion device of claim 16; and a detection mechanism module, configured to detect blood glucose continuously, connected or integrated with the control mechanism module and the infusion mechanism module of the interlocking drug infusion device.

* * * * *